United States Patent [19]
Gal-Or et al.

[11] Patent Number: 5,919,347
[45] Date of Patent: Jul. 6, 1999

[54] METHOD OF ELECTROPHORETIC DEPOSITION OF LAMINATED GREEN BODIES

[75] Inventors: Leah Gal-Or; David Brandon, both of Haifa; Roni Goldner, Mizpe Adi; Liudmilla Cherniak, Haifa; Leonid Perlin, Haifa; Nina Sezin, Haifa; Sonia Liubovich, Haifa, all of Israel

[73] Assignee: Cerel (Ceramic Technologies) Ltd., Nesher, Israel

[21] Appl. No.: 08/839,047

[22] Filed: Apr. 23, 1997

[51] Int. Cl.⁶ ..................................................... C25D 13/02
[52] U.S. Cl. ........................... 204/484; 204/490; 204/491
[58] Field of Search ..................................... 204/490, 491, 204/484

[56] References Cited

U.S. PATENT DOCUMENTS

| | | | |
|---|---|---|---|
| 4,279,725 | 7/1981 | Powers et al. | 204/491 |
| 5,002,647 | 3/1991 | Tanabe et al. | 204/490 |
| 5,194,129 | 3/1993 | Kerkar et al. | 204/181.5 |
| 5,700,361 | 12/1997 | Shiomitsu et al. | 204/490 |
| 5,795,456 | 8/1998 | Friedman et al. | 204/490 |

FOREIGN PATENT DOCUMENTS 58-75711  4/1983  Japan .

OTHER PUBLICATIONS

Chartier, et al, "Laminar Ceramic Composites", *J. Eur. Cer. Soc.*, 15 (1995) 101–107. no month available.

Nicholson et al, "Electrophoretic Deposition and its use to Synthesize $ZrO_2/Al_2O_3$ Microlaminate Ceramic/Ceramic Composites", *J. of Material Science*, 28 (1993) 6274–6278. no month available.

Sakar, P., "Electrophoretic Deposition and Its Use to Synthesize $Al_2O_3$/YSZ Microlaminate Ceramic/Ceramic Composites", *Ceram. Eng. Sci. Proc.*, 14 [9–10], 707–16 (1993). no month available.

Sakar et al, "Structural Ceramic Microlaminates by Electrophoretic Deposition", *J. Am. Ceramic Soc.*, vol. 75, No. 10, pp. 2907–2909, (1992). no month available.

Woolf et al, "Fabrication of Long Length Bi–2223 Superconductor Tape Using Continuous Electrphoretic Deposition on Round and Flat Substrates", *J. of Electronic Masterials*, vol. 24, No. 12, pp. 1797–1801, (1995). no month available.

Ishihara et al, "Preparation of Yttria–Stabilized Zirconia Films for Solid Oxide Fuel Cells by Electrophoretic Deposition Method", *Chemistry Letters (Japan)*, pp. 943–946, (1992). no month available.

Whitehead et al, "Non–Planar $Al_2O_3$/UPSZ Laminates by Electrophoretic Deposition Using $Al_2O_3$ Fibre Electrodes", No ref given. (no date available).

Andrews et al, "The Forming of Ceramic Bodies by Electrophoretic Deposition", *Proc. Brit. Ceramic Soc.*, pp. 211–229, (1968). no month available.

Brownie et al, "Electrophoretic Deposition of Ceramic Sol Particles on Ceramic Substrates" *Ceram. Eng. Sci. Proc.*, 14(9–10), pp. 707–716, (1993). no month available.

*Primary Examiner*—Kishor Mayekal
*Attorney, Agent, or Firm*—Mark M. Friedman

[57] ABSTRACT

A method of electrophoretic deposition of a ceramic green body. A ceramic powder is optionally washed with a polar solvent such as deionized water, dried, and suspended in a polar organic solvent in a proportion of at least 20% by weight. A positive surface charge is imposed on the suspended particles by conventional means such as ball milling or ultrasonic treatment. A green body is deposited on a cathode by passing a direct electric current of constant current density through the suspension. The density of the green body generally is at least 70% of theoretical. The density of the fired body generally is at least 98% of theoretical. A layered green body may be deposited by using several suspensions of differing global ceramic composition and depositing each microlayer in a different suspension.

15 Claims, No Drawings

METHOD OF ELECTROPHORETIC DEPOSITION OF LAMINATED GREEN BODIES

FIELD AND BACKGROUND OF THE INVENTION

The present invention relates to electrophoretic deposition and, more particularly, to a method for the electrophoretic deposition of monolithic and laminated green bodies.

Precisely shaped, small ceramic bodies are used in many applications, including as pitch bonding capillaries in microelectronics, as high temperature nozzles, as ferrules for connecting optical fibers, as high temperature engine components, as dental crowns and as bearing parts. To achieve the precise shaping required for the first application, bonding capillaries, it has been necessary to use the process of cold pressing to fabricate ceramic capillaries.

Multilayer ceramic laminates, made of sequential layers of ceramics such as alumina and zirconia, are known in a variety of geometric shapes, including plates and discs. Applications of ceramic laminates include mechanical seals, automotive engine parts, furnace elements, multilayer and FGM substrates for hybrid circuits, capacitors, RF filters, and microwave components. The processes used to fabricate ceramic laminates include chemical vapor deposition (CVD) and physical vapor deposition (PVD), for layers less than about 1 micron in thickness; tape casting, for layers thicker than about 100 microns; and electrophoretic deposition (EPD), for layers between about 1 micron and about 100 microns in thickness, as will now be described.

Electrophoresis is a process in which charged ceramic particles suspended in a liquid medium are attracted to an electrode when an electrical field is imposed on the particles. EPD is the process of depositing a body of a desired shape on an electrode, using electrophoresis. EPD has long been used to form green ceramic bodies. In particular, EPD has been used by Sarkar, Haung and Nicholson (Electrophoretic deposition and its use to synthesize $Al_2O_3$/YSZ microlaminate ceramic composites, *Ceram. Eng. Sci. Proc.* vol. 14 pp. 707–716 (1993)) to deposit laminated composites of alumina and yttria-stabilized zirconia (YSZ).

There is thus widely recognized need for, and it would be highly advantageous to have, a method of EPD that can be used in the fabrication of small, precisely shaped ceramic bodies such as connecting ferrules, orifices and micro-tubes.

SUMMARY OF THE INVENTION

According to the present invention, there is provided a method for electrophoretic deposition of ceramic particles as a green body, including the steps of: (a) forming a first suspension of the ceramic particles in a first polar organic solvent, the ceramic particles constituting at least about 20% of the first suspension by weight; and (b) passing a first direct electrical current through the first suspension, using a deposition electrode.

According to the present invention, there is provided a green body formed of ceramic particles and having a green density of at least 70% of theoretical.

According to the present invention, there is provided a laminated ceramic body including alternating layers of a first composition and a second composition, the first composition having a higher proportion of alumina and a lower proportion of zirconia than the second composition, each of the layers of the first composition having a thickness between about 20 microns and about 40 microns, and each of the layers of the second composition having a thickness between about 30 microns and about 50 microns.

In the formation of ceramic green bodies by EPD, the ceramic particles may be positively charged, in which case they are deposited on the cathode; or they may be negatively charged, in which case they are deposited on the anode. The electrode on which the ceramic particles are deposited is referred to herein as the "deposition electrode". In the examples given herein, the deposition electrode is the cathode, but it will be understood that the scope of the present invention includes the deposition by EPD of negatively charged ceramic particles, so that the deposition electrode is the anode. A small ceramic article such as a bonding capillary or a micro-tube is formed by deposition on a deposition electrode having an external shape identical to the desired internal shape of the capillary. The green body must be sufficiently dense and rigid to retain its shape as it is removed from the deposition electrode and prepared for sintering. To achieve the necessary mechanical strength, the green body may be deposited on the deposition electrode in microlayers, as taught by Sarkar, Haung and Nicholson. This alone, however, is insufficient to give the green body the required rigidity.

Sarkar, Haung and Nicholson used suspensions that included up to 10% by weight of ceramic in polar organic liquids such as ethanol, and obtained green bodies with densities of about 60% of theoretical. Surprisingly, it has been found that using denser suspensions, including from about 20% to about 70% by weight of ceramic, allows the deposition by EPD of both laminated and monolithic green bodies, with densities of 70% and higher of theoretical, that retain their shape when removed from the deposition electrode and sintered. To achieve this green body density in a monolithic green body, it is necessary first to wash the ceramic powders repeatedly in a polar solvent such as deionized water, until the conductivity of the used washing solvent is essentially the same as the original conductivity of the washing solvent. The utility of this washing step in the production of denser monolithic green bodies is believed to be related to the consequent reduction in the ionic conductivity of the suspension. This washing step is optional in the case of laminated green bodies. Preferably, the washed powders are dried before being added to the polar organic solvent to form the suspension.

Suspensions and slurries with higher concentrations of ceramic particles have been used to form green bodies by tape casting. For example, Chartier, Merle and Besson (Laminar ceramic composites, *J. Eur. Ceram. Soc.* Vol. 15 pp. 101–107 (1995)) used a slurry of greater than 60% ceramic in an azeotropic mixture of methyl ethyl ketone and ethanol to form alumina-zirconia laminates by tape casting. Tape casting is not suitable for fabricating the ceramic bodies of the present application, because, as noted above, tape casting is restricted in practice to layers thicker than about 100 microns, and to flat geometries. Kerkar et al., in U.S. Pat. No. 5,194,129, teach the manufacture of optical ferrules by EPD, using aqueous suspensions of ceramic particles that contained about 40% to 50% by weight of ceramic. Aqueous suspensions are not suitable for the present application because they are subject to electrolysis, leading to the formation of hydrogen bubbles at the cathode and a consequent decrease in the density and local uniformity of a green body deposited thereon.

A laminated green body is formed by EPD by using two or more suspensions of differing global compositions, and alternately placing the electrodes in each of the suspensions, until the desired number of microlayers is deposited. By "global composition" is meant the composition of the ceramic component of the suspension taken as a whole. For example, a suspension of 80% $Al_2O_3$ and 20% $ZrO_2$ has a different global composition than a suspension of 40% $Al_2O_3$ and 60% $ZrO_2$, even though the individual $Al_2O_3$ and $ZrO_2$ particles of the two suspensions are identical in composition. The microlayers are deposited at a constant current density, as taught by Sarkar, Haung and Nicholson, in order to achieve a constant rate of deposition.

The method of the present invention confers the following advantages on the resulting ceramic bodies:

Precisely controlled shape

Uniform and parallel layers in laminates

High strength and toughness, in the case of multilayer laminates

Fine, stress-free microstructure

Near net shaped products

In addition, the method is more cost effective and less wasteful of raw materials than other methods known in the art, is environment-friendly and can be automated in a straightforward manner.

DESCRIPTION OF THE PREFERRED EMBODIMENTS

The present invention is of a method of electrophoretic deposition that can be used to form green bodies of precisely controlled shapes. Specifically, the present invention can be used in the fabrication of pitch bonding capillaries.

The principles and operation of electrophoretic deposition according to the present invention may be better understood with reference to the following description.

The scope of the present invention includes particles of all suitable ceramics, both oxides and non-oxides. Non-limitative examples of suitable ceramics include alumina, zirconia (including YSZ, CESZ and MGSZ), titania, baria and mixtures thereof, such as zirconia-toughened alumina and alumina-toughened zirconia. The particles should be small enough (less than about 1 micron across) to produce a uniform deposit on the cathode.

The preferred polar organic solvents are pure ethanol, pure methyl ethyl ketone and mixtures of ethanol and methyl ethyl ketone in ratios of between 50:50 and 80:20. The most preferred solvent is the 60:40 azeotrope of ethanol and methyl ethyl ketone.

To impose the needed positive surface charge on the ceramic particles, the suspension is ball milled, using ceramic grinding media, for up to 24 hours, or subjected to 20 KHz ultrasound at a power level of up to about 550 watts, for between about 2 minutes and about 15 minutes. Optionally, additives such as pH adjustment agents, dispersants and binders are added to the suspension. The pH adjustment agent can be any suitable organic or inorganic acid that is miscible in the polar organic solvent. The preferred pH adjustment agents are hydrochloric acid and acetic acid. The preferred dispersants are acetylacetone and chloracetic acid, which have been found to allow the deposition, in laminated green bodies, of relatively smooth ceramic microlayers as thick as about 100 microns, in contrast to the prior art microlayer thicknesses of no more than about 20 microns. It should be noted that the preferred microlayer thicknesses, to provide alumina-zirconia laminates of alternating alumina-rich and zirconia-rich layers with maximum strength and toughness, are between about 20 microns and about 40 microns, for the alumina-rich layer, and between about 30 microns and about 50 microns for the zirconia-rich layer. The preferred binders are polyvinyl butyral, nitrocellulose and shellac.

The principle criteria for selecting electrode materials is that they be inert under process conditions and inhibit the evolution of hydrogen gas. If the deposition electrode is a cathode, it may be either consumable or reusable. A consumable cathode is one that is destroyed during the sintering process, so that the green body need not be removed from the cathode before sintering. The preferred materials for a consumable cathode are carbon and electrically conducting polymers. The preferred materials for a reusable cathode arc stainless steel, nickel, aluminum, tungsten carbide and noble metals such as platinum, palladium, silver and gold, and their alloys. The preferred materials for the anode are nickel and noble metals. As noted above, in the production of small ceramic articles such as micro-tubes, the cathode is a wire having a shape identical to the desired interior shape of the ceramic article. Preferably, the anode surrounds the cathode.

Also as noted above, it is necessary to inhibit the production of hydrogen gas at the cathode. In addition to using a polar organic solvent instead of water to form the suspension, this is accomplished by including a hydrogen getter and/or a surface coating on the cathode to absorb hydrogen. Preferred hydrogen getters include palladium and platinum and their alloys. In the case of stainless steel cathodes, a surface coating of a fibrous material such as lens paper has been found by us to be effective for both absorption of hydrogen and facilitating the removal of the green body from the cathode subsequent to the deposition. Removal of the green body from the cathode also is facilitated by polishing the cathode surface before deposition.

The anode and cathode are immersed in the suspension, and a direct electrical current of constant current density, as measured at the cathode, is passed between the electrodes while the suspension is stirred. The preferred range of current densities is between about 0.1 $mA/cm^2$ and about 5 $mA/cm^2$. As noted above, to deposit a laminated green body, several suspensions of differing global composition are used, and the electrodes are moved from one suspension to another as necessary. The deposition time in each suspension depends on the desired microlayer thickness, the current density and the suspension concentration. Typical deposition times for one microlayer range from a few seconds to a few minutes. The total deposition time for a planar laminated green body is on the order of a few hours. The total deposition time for a monolithic or laminated cylindrical body, such as a pitch bonding capillary, having a diameter of a few millimeters is on the order of one minute or less.

Following the deposition, the green body is removed from the cathode, dried in a dessicator, and sintered. Pressureless sintering in air at about 1550° C. for a few hours has been found suitable for the production of stress-free alumina-zirconia laminates. The sintered ceramic body may be machined and/or polished after sintering.

EXAMPLE 1

Multilayer Laminate

A first suspension was prepared by dispersing 270 grams of alumina powder (average particle size 0.4 microns) and 30 grams of zirconia powder (average particle size 0.3 microns) in 1000 ml of an azeotropic mixture of ethanol and methyl ethyl ketone. A second suspension was prepared by dispersing 160 grams of the same alumina powder and 240 grams of the same zirconia powder in 1000 ml of an azeotropic mixture of ethanol and methyl ethyl ketone.

Both suspensions were prepared using 800 ml of the ethanol-methyl ethyl ketone mixture in each, and ball milled for 24 hours, using alumina balls to mill the first suspension and zirconia balls to mill the second suspension. 200 more ml of the ethanol-methyl ethyl ketone mixture was added to each suspension, to bring the total volume of solvent up to the desired 1000 ml. Enough HCl was added to each suspension to adjust the pH of the first suspension to about 7 and the pH of the second suspension to about 6. About 0.5% by volume of acetylacetone dispersant was added to the first suspension. About 1.5% by volume of acetylacetone dispersant was added to the second suspension. About 0.1% by volume of shellac binder was added to each suspension. Each suspension now was transferred to its own electrophoretic cell.

The cathode was a stainless steel plate covered with Wattman lens paper. Each electrophoretic cell was provided with its own half-cylinder nickel anode about 40 mm in radius. The cathode was placed in the first electrophoretic cell at the center of curvature of the anode, and a direct electrical current having a current density of about 0.4 mA/cm$^2$ was passed between the electrodes for about 45 seconds. The cathode then was removed from the first electrophoretic cell and placed in the second electrophoretic cell, at the same location as before relative to the anode, and the same 0.4 mA/cm$^2$ of direct electrical current was run between them. This process was repeated for 50 cycles, resulting in the deposition of 100 microlayers, each about 50 microns thick, for a total laminate thickness of about 5 millimeters. A final 50 micron alumina-rich microlayer was deposited in the first electrophoretic cell. The green body was removed from the cathode, dried in a dessicator for a few hours, and sintered in air at 1550° C. for 4 hours. The green body had a density of about 70% of theoretical. The sintered body had an open porosity of between 0.2% and 0.5% by volume. The microhardness of the alumina-rich microlayers, measured by the Vickers method, was about 2400 kg/cm$^2$. The microhardness of the zirconia-rich layers was about 2000 kg/cm$^2$. The bending strength of the sintered body was about 80 kg/mm$^2$.

EXAMPLE 2

Monolithic Capillary 45 grams of alumina (average particle size 0.4 microns to 0.5 microns) and 5 grams of zirconia (average particle size 0.3 microns) were washed repeatedly with deionized water until the conductivity of the wash water fell to about 5 microsiemens/cm. The powders were dried, and enough ethanol was added to bring the total volume to 100 ml. The resulting suspension was ball milled for 4 hours. 0.025 ml of acetylacetone dispersant and 2 ml of a 5% by volume solution of shellac binder in ethanol were added. The suspension was stirred for about 15 minutes and transferred to an electrophoretic cell.

Two different cathodes were used in two different runs: a graphite wire and a tungsten carbide wire having external shapes identical to the internal shape of a typical bonding capillary, tapering from a 1.2 millimeter diameter at the distal end to a 0.04 millimeter diameter at the proximal end. The cathode was a nickel cylinder about 60 mm in diameter surrounding the cathode. The electrodes were placed in the electrophoretic cell and a direct electrical current having a current density of about 1.0 mA/cm$^2$ was run between them for about 60 seconds, resulting in the deposition of a 1 millimeter thick deposit. The density of the deposited green bodies was about 70% of theoretical. The green body on the tungsten carbide cathode was removed, and the green bodies were sintered in air at 1550° C. for about 1.5 hours, yielding alumina capillaries with densities of 99% of theoretical and microhardness of 2500 kg/cm$^2$.

While the invention has been described with respect to a limited number of embodiments, it will be appreciated that many variations, modifications and other applications of the invention may be made.

What is claimed is:

1. A method for electrophoretic deposition of ceramic particles as a green body, comprising the steps of:
    (a) forming a first suspension of the ceramic particles in a first polar organic solvent, the ceramic particles constituting at least about 20% of said first suspension by weight;
    (b) passing a first direct electrical current through said first suspension, using a cathode having a fibrous surface coating thereon for absorbing hydrogen;
    (c) forming a second suspension of the ceramic particles in a second polar organic solvent, the ceramic particles constituting at least about 20% of said second suspension by weight, the ceramic particles of said second suspension having a different global composition than the ceramic particles of said first suspension; and
    (d) passing a second direct electrical current through said second suspension, using said cathode.

2. The method of claim 1, wherein said first direct electrical current and said second direct electrical current have constant current densities.

3. The method of claim 2, wherein said current densities of said first and second direct electrical currents are between about 0.1 mA/cm$^2$ and about 5 mA/cm$^2$.

4. The method of claim 1, further comprising the step of:
    (e) washing said ceramic particles in a polar solvent, prior to said forming of said first suspension and said second suspension.

5. The method of claim 4, wherein said polar solvent includes deionized water.

6. The method of claim 1, wherein said cathode is made of a material selected from the group consisting of carbon, electrically conducting polymers, stainless steel, nickel, aluminum, noble metals and tungsten carbide.

7. The method of claim 1, wherein said first direct electrical current is passed between said cathode and an anode made of a material selected from the group consisting of noble metals and nickel.

8. The method of claim 1, wherein at least one of said polar organic solvents includes at least one alcohol.

9. The method of claim 1, wherein at least one of said polar organic solvents includes at least one ketone.

10. The method of claim 1, further comprising the step of:
    (e) selecting the ceramic particles from the group consisting of alumina particles, zirconia particles, yttria-stabilized zirconia particles, ceria-stabilized zirconia particles, magnia-stabilized zirconia particles, titania particles, baria particles, mixed alumina-zirconia particles, mixed alumina-titania particles, mixed zirconia-titania particles, mixed alumina-baria particles, mixed zirconia-baria particles and mixed titania-baria particles.

11. The method of claim 1, further comprising the step of:
    (e) adding a dispersant to at least one of said suspensions.

12. The method of claim 11, wherein said dispersant is selected from the group consisting of acetylacetone and chloracetic acid.

13. A method for electrophoretic deposition of ceramic particles as a green body, comprising the steps of:

(a) forming a suspension of the ceramic particles in a polar organic solvent; and
(b) passing a direct electrical current through the suspension, using a deposition electrode having a fibrous surface coating thereon for absorbing evolved gas.

14. The method of claim 13, wherein said deposition electrode is a cathode, and wherein said evolved gas is hydrogen.

15. The method of claim 13, wherein said ceramic particles constitute at least 20% of said suspension by weight.

* * * * *